(12) United States Patent
Jacobson et al.

(10) Patent No.: US 8,986,723 B2
(45) Date of Patent: Mar. 24, 2015

(54) OIL FORMULATIONS COMPRISING CYLCOPROPENE COMPOUNDS

(75) Inventors: Richard M. Jacobson, Chalfont, PA (US); Yueqian Zhen, Paoli, PA (US)

(73) Assignee: Rohm and Haas Company, Philadelphia, PA (US)

( * ) Notice: Subject to any disclaimer, the term of this patent is extended or adjusted under 35 U.S.C. 154(b) by 290 days.

(21) Appl. No.: 13/581,532

(22) PCT Filed: Feb. 9, 2011

(86) PCT No.: PCT/US2011/024120
§ 371 (c)(1),
(2), (4) Date: Sep. 26, 2012

(87) PCT Pub. No.: WO2011/109144
PCT Pub. Date: Sep. 9, 2011

(65) Prior Publication Data
US 2013/0065764 A1     Mar. 14, 2013

Related U.S. Application Data

(60) Provisional application No. 61/309,073, filed on Mar. 1, 2010.

(51) Int. Cl.
| | | |
|---|---|---|
| *A61K 9/14* | (2006.01) | |
| *A61K 9/50* | (2006.01) | |
| *A01N 25/26* | (2006.01) | |
| *A01N 27/00* | (2006.01) | |
| *A01N 25/04* | (2006.01) | |

(52) U.S. Cl.
CPC ............... *A01N 27/00* (2013.01); *A01N 25/04* (2013.01)
USPC ........... 424/408; 424/451; 424/463; 424/489; 424/490; 504/100; 504/357

(58) Field of Classification Search
CPC .............................. A01N 27/00; A01N 25/04
See application file for complete search history.

(56) References Cited

U.S. PATENT DOCUMENTS

| 6,017,849 A | 1/2000 | Daly et al. | |
|---|---|---|---|
| 2009/0035380 A1* | 2/2009 | Kostansek | .................... 424/498 |
| 2009/0286911 A1 | 11/2009 | Brick et al. | |

FOREIGN PATENT DOCUMENTS

| CN | 101356917 | | 2/2009 |
|---|---|---|---|
| CN | 102307472 | | 11/2012 |
| EP | 1782692 | | 5/2007 |
| EP | 2020177 | | 2/2009 |
| EP | 2020177 | A1 | 2/2009 |
| EP | 2158812 | | 3/2010 |
| TW | 2009/06298 | | 2/2009 |
| WO | 2010/080891 | | 7/2010 |
| WO | 2010/080891 | A1 | 7/2010 |
| WO | WO 2010080891 | * | 7/2010 |

OTHER PUBLICATIONS

PCT International Search Report issued by the ISA/US in connection with PCT/US2011/024120 and completed on Apr. 20, 2011.

* cited by examiner

*Primary Examiner* — Alton Pryor
(74) *Attorney, Agent, or Firm* — Yung H. Lee; Barnes & Thornburg LLP.

(57) ABSTRACT

A composition comprising (a) a non-aqueous pourable fluid, (b) droplets dispersed in said pourable fluid (a), wherein said droplets comprise (i) a non-aqueous continuous phase that is a solid or that is a liquid of high viscosity and (ii) solid particles dispersed in said continuous phase (i), wherein said solid particles (ii) have median size as measured by the largest dimension of 100 micrometers or less, and wherein said solid particles (ii) comprise one or more cyclopropene compound and one or more molecular encapsulating agent. Also, a method of treating plants or plant parts involving bringing such a composition into contact with plants or plant parts.

9 Claims, No Drawings

OIL FORMULATIONS COMPRISING CYLCOPROPENE COMPOUNDS

CROSS REFERENCE TO RELATED APPLICATIONS

This application is a U.S. national stage application of international application serial No. PCT/US2011/024120 filed Feb. 9, 2011, which claims the benefit of priority under 35 U.S.C. 119(e) of U.S. Provisional Patent Application No. 61/309,073 filed on Mar. 1, 2010. The entire disclosures of PCT/US2011/024120 and U.S. Provisional Patent Application No. 61/309,073 are hereby incorporated by reference.

This application claims the benefit of priority under 35 U.S.C. §119(e) of U.S. Provisional Patent Application No. 61/309,073 filed on Mar. 1, 2010.

BACKGROUND

A convenient way of storing and transporting cyclopropene compounds is in the form of complexes with molecular encapsulating agents. Such a complex is useful, for example, for use in treating plants or plant parts by contacting the plants or plant parts with the complex in order to bring about contact between the plants or plant parts and the cyclopropene. Such treatment of plants or plant parts is often effective at desirably interrupting one or more ethylene-mediated process in the plants or plant parts. For example, such treatment of plant parts can sometimes desirably delay unwanted ripening. For another example, such treatment of crop plants prior to harvest can sometimes improve the yield of the crop.

US Patent Application Publication 2009/0035380 discloses an oil medium with particles dispersed in that oil medium, and the particles contain cyclopropene compound and molecular encapsulating agent. The oil described by US 2009/0035380 is a liquid that is not water. Generally, such an oil easily allows the dispersed particles to diffuse to the boundary between the oil and air or water. When such a particle encounters such a boundary, the result is often premature release of the cyclopropene compound from the particle.

It is desired to provide a composition in which particles that contain cyclopropene compound and molecular encapsulating agent are dispersed in a non-aqueous continuous phase, where the composition does not allow such easy diffusion of the particles to the boundary of the non-aqueous continuous phase. It is contemplated that such a composition would be useful for treating plants or plant parts, either by bringing the composition itself into contact with plants or plant parts or by dispersing the composition in a diluent such as, for example, water, and then bringing the resultant dispersion into contact with plants or plant parts.

STATEMENT OF THE INVENTION

In one aspect of the present invention, there is provided a composition that contains:
(a) a non-aqueous pourable fluid,
(b) droplets dispersed in said pourable fluid (a), wherein said droplets comprise
   (i) a non-aqueous continuous phase that is a solid or that is a liquid of high viscosity and
   (ii) solid particles dispersed in said continuous phase (i), wherein said solid particles (ii) have median size as measured by the largest dimension of 100 micrometers or less, and wherein said solid particles (ii) comprise one or more cyclopropene compound and one or more molecular encapsulating agent.

In another aspect of the present invention, there is a method of treating plants or plant parts that includes the step of bringing such a composition into contact with the plants or plant parts.

DETAILED DESCRIPTION

As used herein, a "fluid" is a material (which may be a single compound or a mixture of compounds) that is liquid at 25° C. and 1 atmosphere pressure and that has a boiling point at 1 atmosphere pressure of 30° C. or higher. As used herein, a fluid is "non-aqueous" if it contains, by weight based on the weight of the fluid, 10% water or less. As used herein, a fluid is "pourable" if it has viscosity at 25° C. at shear rate of 0.01 $sec^{-1}$ of 1 Pa*s (10 Poise) or less.

By "dispersed" herein is meant that discrete masses of one material (the "dispersed" material, which may be in any divided form such as, for example, liquid droplets or solid particles) are distributed throughout a second material, which forms a continuous medium around the particles. The system of discrete masses dispersed in the continuous medium is known herein as a "dispersion." Each distributed discrete mass of the dispersed material has multiple molecules of the dispersed material. Typically, the discrete masses of the dispersed material have median particle size of 10 nanometers or larger.

As defined herein, a "dispersant" is a compound that is capable of assisting discrete masses to form a stable dispersion in a continuous medium. In the dispersion, some or all of the dispersant resides on or near the surface of the discrete masses.

As defined herein, a substance ("solute") is said to be dissolved in another substance ("solvent") if individual molecules of the solute are distributed throughout the solvent.

As defined herein, a substance ("S1") is said to be not soluble in a second substance ("S2") if, when a mixture is made of 10 grams of S1 for every 100 grams of S2, the amount of S1 that dissolves in S2 is less than 1 gram of S1 for every 100 grams of S2.

As defined herein, an aqueous medium is a fluid that contains 50% or more water by weight based on the weight of that fluid.

A compound is organic if it contains carbon and if it is not a compound normally considered to be inorganic such as carbon oxides, carbides, carbon disulfide, metallic cyanides, metallic carbonyls, phosgene, carbonyl sulfide, and others.

As used herein the "cloud point" is the temperature of a mixture above which all the ingredients are dissolved, usually forming a clear solution, and below which some or all of one or more of the ingredients becomes dispersed rather than dissolved in the solvent, forming a mixture with a cloudy appearance.

Vinyl polymers are the result of polymerization of the carbon-carbon double bonds of ethylenically unsaturated monomers. Vinyl polymers may be homopolymers (in which every repeat unit is the same) or may be copolymers (which contain two or more different repeat units).

As used herein, a "fatty group" is a chemical group that contains at least one chain of carbon atoms that is at least 8 carbon atoms long. A "fatty compound" is any compound that contains a fatty group.

The practice of the present invention involves the use of one or more cyclopropene compound. As used herein, a cyclopropene compound is any compound with the formula

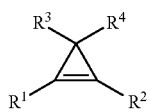

where each $R^1$, $R^2$, $R^3$ and $R^4$ is independently selected from the group consisting of H and a chemical group of the formula:

-(L)$_n$-Z where n is an integer from 0 to 12. Each L is a bivalent radical. Suitable L groups include, for example, radicals containing one or more atoms selected from H, B, C, N, O, P, S, Si, or mixtures thereof. The atoms within an L group may be connected to each other by single bonds, double bonds, triple bonds, or mixtures thereof. Each L group may be linear, branched, cyclic, or a combination thereof. In any one R group (i.e., any one of $R^1$, $R^2$, $R^3$ and $R^4$) the total number of heteroatoms (i.e., atoms that are neither H nor C) is from 0 to 6. Independently, in any one R group the total number of non-hydrogen atoms is 50 or less. Each Z is a monovalent radical. Each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system.

The $R^1$, $R^2$, $R^3$, and $R^4$ groups are independently selected from the suitable groups. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted.

Among the suitable $R^1$, $R^2$, $R^3$, and $R^4$ groups are, for example, aliphatic groups. Some suitable aliphatic groups include, for example, alkyl, alkenyl, and alkynyl groups. Suitable aliphatic groups may be linear, branched, cyclic, or a combination thereof. Independently, suitable aliphatic groups may be substituted or unsubstituted.

As used herein, a chemical group of interest is said to be "substituted" if one or more hydrogen atoms of the chemical group of interest is replaced by a substituent.

Also among the suitable $R^1$, $R^2$, $R^3$, and $R^4$ groups are, for example, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, for example, substituted and unsubstituted heterocyclic groups that are connected to the cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, for example, hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl, butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl; and substituted analogs thereof.

As used herein, the chemical group G is a 3 to 14 membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring systems suitable as chemical group G may be monocyclic, bicyclic, tricyclic, polycyclic, spiro, or fused; among suitable chemical group G ring systems that are bicyclic, tricyclic, or fused, the various rings in a single chemical group G may be all the same type or may be of two or more types (for example, an aromatic ring may be fused with an aliphatic ring).

In some embodiments, one or more of $R^1$, $R^2$, $R^3$, and $R^4$ is hydrogen or ($C_1$-$C_{10}$) alkyl. In some embodiments, each of $R^1$, $R^2$, $R^3$, and $R^4$ is hydrogen or ($C_1$-$C_8$) alkyl. In some embodiments, each of $R^1$, $R^2$, $R^3$, and $R^4$ is hydrogen or ($C_1$-$C_4$) alkyl. In some embodiments, each of $R^1$, $R^2$, $R^3$, and $R^4$ is hydrogen or methyl. In some embodiments, $R^1$ is ($C_1$-$C_4$) alkyl and each of $R^2$, $R^3$, and $R^4$ is hydrogen. In some embodiments, $R^1$ is methyl and each of $R^2$, $R^3$, and $R^4$ is hydrogen, and the cyclopropene compound is known herein as "1-MCP."

In some embodiments, a cyclopropene compound is used that has boiling point at one atmosphere pressure of 50° C. or lower; or 25° C. or lower; or 15° C. or lower. Independently, in some embodiments, a cyclopropene compound is used that has boiling point at one atmosphere pressure of −100° C. or higher; −50° C. or higher; or −25° C. or higher; or 0° C. or higher.

The composition of the present invention includes at least one molecular encapsulating agent. In some embodiments, at least one molecular encapsulating agent encapsulates one or more cyclopropene compound or a portion of one or more cyclopropene compound. A complex that contains a cyclopropene compound molecule or a portion of a cyclopropene compound molecule encapsulated in a molecule of a molecular encapsulating agent is known herein as a "cyclopropene compound complex."

In some embodiments, at least one cyclopropene compound complex is present that is an inclusion complex. In such an inclusion complex, the molecular encapsulating agent forms a cavity, and the cyclopropene compound or a portion of the cyclopropene compound is located within that cavity.

Independently, in some of such inclusion complexes, the interior of the cavity of the molecular encapsulating agent is substantially apolar or hydrophobic or both, and the cyclopropene compound (or the portion of the cyclopropene compound located within that cavity) is also substantially apolar or hydrophobic or both. While the present invention is not limited to any particular theory or mechanism, it is contemplated that, in such apolar cyclopropene compound complexes, van der Waals forces, or hydrophobic interactions, or both, cause the cyclopropene compound molecule or portion thereof to remain within the cavity of the molecular encapsulating agent.

The amount of molecular encapsulating agent can usefully be characterized by the ratio of moles of molecular encapsulating agent to moles of cyclopropene compound. In some embodiments, the ratio of moles of molecular encapsulating agent to moles of cyclopropene compound is 0.1 or larger; or 0.2 or larger; or 0.5 or larger; or 0.9 or larger. Independently, in some of such embodiments, the ratio of moles of molecular encapsulating agent to moles of cyclopropene compound is 10 or lower; or 5 or lower; or 2 or lower; or 1.5 or lower.

Suitable molecular encapsulating agents include, for example, organic and inorganic molecular encapsulating agents. Suitable organic molecular encapsulating agents include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In some embodiments, the encapsulating agent is alpha-cyclodextrin, beta-cyclodextrin, gamma-cyclodextrin, or a mixture thereof. In some embodiments of the invention, alpha-cyclodextrin is used. The preferred encapsulating agent will vary depending upon the structure of the cyclopropene compound or cyclopropene compounds being used. Any cyclodextrin or mixture of cyclodextrins, cyclodextrin polymers, modified cyclodextrins, or mixtures thereof can also be utilized pursuant to the present invention.

In the practice of the present invention, a non-aqueous pourable fluid (herein called "fluid (a)") is used.

In some embodiments, fluid (a) contains one or more organic compounds. An organic compound contained in fluid (a) is known herein as a "first" organic compound. Some suitable first organic compounds are liquid at 25° C. and 1 atmosphere pressure and have a boiling point at 1 atmosphere pressure of 30° C. or higher.

Some suitable first organic compounds have viscosity at 25° C. and shear rate of 0.01 sec$^{-1}$ of 1 Pa*sec (10 Poise) or lower; or 0.1 Pa*sec (1 Poise) or lower; or 0.01 Pa*sec (0.1 Poise) or lower. Also contemplated are mixtures of two or more first organic compounds, where the mixture has viscosity at 25° C. and shear rate of 0.01 sec$^{-1}$ of 1 Pa*sec (10 Poise) or lower; or 0.1 Pa*sec (1 Poise) or lower; or 0.01 Pa*sec (0.1 Poise) or lower.

Some suitable first organic compounds are polar compounds. Some suitable first organic compounds have dipole moment (in Debye units) of 2.5 or greater; or 3 or greater; or 3.5 or greater. Independently, some suitable first organic compounds have no hydrogen atom bonded to an electronegative atom. Some suitable first organic compounds have no hydrogen atom bonded to an oxygen, nitrogen, or sulfur atom. In some embodiments, a first organic compound is used in which every hydrogen atom is bonded to a carbon atom.

Some suitable first organic compounds include, for example, dialkyl ketones, alkylene carbonates, nitroalkanes, and mixtures thereof. In some embodiments, the first organic compound contains ethylene carbonate, propylene carbonate, butylene carbonate, or a mixture thereof. In some embodiments, the first organic compound contains propylene carbonate.

In some embodiments, the amount of first organic compound in the non-aqueous pourable fluid (a) is, by weight based on the weight of the non-aqueous pourable fluid (a), 60% or more; or 75% or more; or 90% or more; or 95% or more. In some embodiments, the sum of the weights of all alkylene carbonates present in the non-aqueous fluid (a) is, by weight based on the weight of the non-aqueous pourable fluid (a), 60% or more; or 75% or more; or 90% or more; or 95% or more. As used herein, "the weight of the non-aqueous pourable fluid (a)" means the weight of the fluid (a) itself, including the weight of any substances (if any) that are dissolved in the fluid (a), and not including the weight of any materials (such as, for example, droplets (b)) dispersed in fluid (a).

In the composition of the present invention, droplets (known herein as "droplets (b)") are dispersed in fluid (a). Droplets (b) contain a continuous phase (known herein as "continuous phase (i)") that is solid or that is a liquid that has high viscosity. Droplets (b) also contain solid particles (known herein as "solid particles (ii)") that are dispersed in continuous phase (i). Continuous phase (i) is considered to be "continuous" because, within a single droplet (b), the continuous phase (i) has the solid particles (ii) dispersed within it. It is contemplated that the mass of continuous phase (i) that is located in one droplet (b) will be isolated from other masses of continuous phase (i) that are located in other droplets (b), separated by intervening fluid (a).

In some embodiments, continuous phase (i) is solid. That is, it is a solid at 25° C. In some embodiments, continuous phase (i) is a liquid that has high viscosity. As used herein, a liquid that has high viscosity is a composition that is liquid at 25° C. and that has viscosity at 25° C. at shear rate of 0.01 sec$^{-1}$ of 25 Pa*s (250 Poise) or more.

In some embodiments, continuous phase (i) contains one or more organic compounds (known herein as a "second organic compounds"). In some embodiments, one or more second organic compound is used that is a solid at 25° C. or else is a liquid that has viscosity at 25° C. at shear rate of 0.01 sec$^{-1}$ of 25 Pa*s (250 Poise) or more. In some embodiments, one or more second organic compound is used that has melting point of 50° C. or higher. In some embodiments, one or more second organic compound is used that is a liquid that has viscosity at 25° C. at shear rate of 0.01 sec$^{-1}$ of 25 Pa*s (250 Poise) or more; or 100 Pa*s (1,000 Poise) or more; or 1,000 Pa*s (10,000 Poise) or more; or 10,000 Pa*s (100,000 Poise) or more.

Among the suitable second organic compounds that are solids at 25° C. or are liquids of high viscosity at 25° C., there are many suitable compositions, including, for example, hydrocarbons, non-hydrocarbon waxes, fatty compounds, organic polymers, and mixtures thereof. Suitable hydrocarbons include, for example, petroleum distillates, hydrocarbon waxes, petroleum jellies, and mixtures thereof. Some suitable hydrocarbon waxes are, for example, polyethylene waxes, microcrystalline waxes, other synthetic waxes, and mixtures thereof. Some suitable non-hydrocarbon waxes include, for example, waxes of biological origin, including, for example, waxes that contain compounds that have the structure of fatty acid esters of fatty alcohols. Some suitable waxes of biological oringin include, for example, beeswax and carnauba wax.

Suitable fatty compounds include, for example, fatty acids, esters of fatty acids, amides of fatty acids, and mixtures thereof. Suitable fatty compounds may be natural products (i.e., products obtained from biological sources), modified natural products, synthetic compounds, or mixtures thereof. Suitable fatty compounds may be pure materials or may be mixtures of fatty compounds. Natural fatty compounds and modified natural fatty compounds are often mixtures. Some suitable modifed natural fatty compounds include, for example, natural fatty compounds that have been hydrogenated, hydroxylated, sulfonated, polymerized, or a combination thereof.

One suitable fatty compound is stearic acid, which may be used in pure form or in the form of a mixture, which may be obtained from a biological source.

One group of suitable fatty compounds are glycerides. Glycerides are mono-, di-, and tri-esters of glycerol. Suitable glycerides are fatty glycerides, which are compounds in which at least one fatty group is attached to the glycerol molecule with an ester linkage. Some suitable glycerides are plant oils (i.e., oils produced by plants) or modified plant oils or a mixture thereof. Some suitable glycerides are, for example, hydrogenated plant oils. Suitable glycerides include, for example, hydrogenated soybean oil and hydrogenated cottonseed oil.

Some compounds that are suitable as the second organic compound are compounds with relatively low dipole moment. In some embodiments, one or more second organic compounds are used that have dipole moment of 1.5 Debye or lower; or 1.0 Debye or lower, or 0.8 Debye or lower. In some embodiments, every second organic compound has dipole moment of 1.5 Debye or lower; or 1.0 Debye or lower, or 0.8 Debye or lower.

In some embodiments, the amount of all second organic compounds in the continuous phase (i) is, by weight based on the weight of the continuous phase (i), is 60% or more; or 75% or more; or 85% or more; or 95% or more; or 99% or more. As used herein, "the weight of the continuous phase (i)" means the weight of the continuous phase (i) itself, including the weight of any substances (if any) that are dissolved in the continuous phase (i), and not including the weight of any materials (such as, for example, solid particles (ii)) dispersed in continuous phase (i).

Among embodiments in which one or more first organic compound is present and in which one or more second organic compound is present, the mixture of all second organic compounds that are present is not soluble (as defined herein above) in the mixture of all first organic compounds that are present. In some embodiments, the mixture of all second organic compounds is not soluble in the mixture of all first organic compounds at 25° C. In some embodiments, the mixture of all second organic compounds is not soluble in the mixture of all first organic compounds over a range of temperatures from 20° C. up to a top temperature, where that top temperature is 40° C. or higher; or 50° C. or higher; or 75° C. or higher.

In some embodiments (herein called "polymer mixture" or "PM" embodiments), the continuous phase (i) contains a mixture (herein called "PM mixture" of an organic polymer and an organic fluid (herein called "PM fluid"). In some PM embodiments, that PM mixture is a solution of the polymer in the PM fluid or a dispersion of the polymer in the PM fluid. In some PM embodiments, the PM mixture is a liquid of high viscosity at 25° C. In some PM embodiments, the PM mixture is a solid (such as, for example, a gel) at 25° C. In some PM embodiments, the PM mixture, at some temperature of 50° C. or higher, is a liquid that has viscosity at 0.01 sec$^{-1}$ of less than 25 Pa*s, and the PM mixture, at 25° C., is either a solid or is a liquid of high viscosity.

In some PM embodiments (herein called "viscosity drop" embodiments), the PM mixture has a low-viscosity temperature range. That is, there is a temperature range over which the viscosity of the PM mixture at 0.01 sec$^{-1}$ is 10 Pa*s or less. In viscosity drop embodiments, the low end of the low-viscosity temperature range is 30° C. or higher, or 50° C. or higher. In viscosity drop embodiments, the high end of the low-viscosity temperature range is 180° C. or lower, or 150° C. or lower, or 100° C. or lower. In viscosity drop embodiments, the PM mixture is a solid or is a liquid of high viscosity over a temperature range that includes the range 18° C. to 28° C. It is contemplated that the PM mixture can be heated into the low-viscosity range for ease of stirring and/or mixing and then cooled or allowed to cool to 25° C. to become a solid or a liquid of high viscosity.

In some viscosity drop embodiments (herein called "cloud point" embodiments), the PM mixture has a cloud point that is higher than 30° C. and lower than 100° C. In some cloud point embodiments, it is possible to heat the PM mixture above the cloud point for convenient stirring and/or mixing (because the PM mixture has viscosity at 0.01 sec$^{-1}$ of less than 10 Pa*s at some temperature above the cloud point) and then to cool the PM mixture below the cloud point, whereupon the PM mixture becomes a solid or a liquid of high viscosity.

In some PM embodiments, the PM fluid contains, for example, one or more hydrocarbon materials. A suitable hydrocarbon material may be a single hydrocarbon substance or may be a mixture of hydrocarbon substances. Some suitable hydrocarbon materials are, when tested in the absence of any dissolved or dispersed solid compounds, liquids with viscosity at 25° C. and shear rate of 0.01 sec$^{-1}$ of 1 Pa*sec (10 Poise) or lower. Some suitable hydrocarbon materials are, for example, petroleum hydrocarbons.

Some PM embodiments contain, for example, one or more vinyl polymer. Suitable vinyl polymers include, for example, polymers and copolymers made from one or more monomers such as, for example, styrene, substituted styrenes, (meth) acrylic acid, esters of (meth)acrylic acid, substituted esters of (meth)acrylic acid, amides of (meth)acrylic acid, substituted amides of (meth)acrylic acid, alkenes, vinyl esters of carboxylic acids, halo-substituted alkenes, and mixtures thereof. Suitable alkenes include, for example, ethylene, propylene, dienes, and mixtures thereof. Suitable vinyl esters of carboxylic acids include, for example, vinyl acetate. In some embodiments, one or more copolymer of ethylene and vinyl acetate is used.

In some PM embodiments, a solvent is used that has dipole moment of 1.5 Debye or lower; or 1.0 Debye or lower, or 0.8 Debye or lower.

In some embodiments, the amount of PM mixture in the continuous phase (i) is, by weight based on the weight of the continuous phase (i) (as defined herein above), is 60% or more; or 75% or more; or 85% or more; or 95% or more; or 99% or more.

Among PM embodiments, the PM fluid is not soluble (as defined herein above) in the mixture of all first organic compounds that are present. In some embodiments, the PM fluid is not soluble in the mixture of all first organic compounds at 25° C. In some embodiments, the PM fluid is not soluble in the mixture of all first organic compounds over a range of temperatures from 20° C. up to a top temperature, where that top temperature is 40° C. or higher; or 50° C. or higher; or 75° C. or higher.

Also contemplated are embodiments in which continuous phase (i) contains a mixture of two or more of the second organic compounds discussed herein above.

In some embodiments, continuous phase (i) is not soluble in pourable fluid (a). In some embodiments, continuous phase (i) is not soluble in pourable fluid (a) at 25° C. In some embodiments, continuous phase (i) is not soluble in pourable fluid (a) over a range of temperatures from 20° C. up to a top temperature, where that top temperature is 40° C. or higher; or 50° C. or higher; or 75° C. or higher.

In the composition of the present invention, droplets (b) also contain solid particles (ii) that are dispersed in continuous medium (i).

The particles of the present invention that are dispersed in continuous medium (i) have median size, as measured by the largest dimension, of 100 micrometer or less. That is, the collection of particles is assessed to determine the size. One suitable method of assessment, for example, is inspection using a microscope. Images of particles, for example, those images obtained in a microscope, may be inspected and assessed by eye, possibly with reference to length standards, or alternatively the images may be inspected and assessed by appropriate image analysis methods, such as, for example, computer programs.

In embodiments in which the particles are not spherical, it is useful to characterize the particles by the largest dimension of each particle. A collection of particles may be characterized by the median value of the largest dimension. That is, half of the particles in the collection, by weight, will have largest dimension that is larger than the median value of the collection. In the practice of the present invention, when the collection of particles dispersed in continuous phase (i) is assessed, that median value is 100 micrometers or less. In some embodiments, particles are used in which that median value is 50 micrometers or less; 20 micrometers or less; or 10 micrometers or less; or 5 micrometers or less; or 2 micrometers or less.

In some embodiments, solid material is manufactured as a powder, but the particle size of that powder is larger than is desirable for use as solid particles (ii). In such embodiments, the powder may be subjected to a process that reduces the particle size. One suitable such process is air milling.

An independent measure of a particle is the aspect ratio, which is the ratio of the largest dimension of the particle to the smallest dimension of the particle. The aspect ratio is independent of the size of the particle. In some embodiments of the present invention, the collection of dispersed particles (ii) dispersed in continuous phase (i) has aspect ratio of 20 or lower; or 10 or lower; or 5 or lower; or 2 or lower.

The dispersed particles (ii) contain cyclopropene compound and molecular encapsulating agent. In some embodiments, some or all of the cyclopropene compound that is present in the composition is part of a cyclopropene compound complex. While the present invention is not limited to any particular theory or model, it is contemplated that most or all of the cyclopropene compound molecules that are present in the composition are present in the form of molecules that are part of cyclopropene compound complexes. It is further contemplated that any cyclopropene compound molecules in the composition that are not part of a cyclopropene compound complex are present, for example, in solution, adsorbed on an interface, some other location, or a combination thereof. In some embodiments, the amount of cyclopropene compound that is present as part of a cyclopropene compound complex, by weight based on the total amount of cyclopropene compound in the composition, is 80% or more; or 90% or more; or 95% or more; or 99% or more.

In some embodiments, dispersed particles (ii) contain only one or more cyclopropene compounds and one or more molecular encapsulating agents. In some embodiments, dispersed particles (ii) contain one or more additional compounds. When additional compounds are present, they may be incorporated into the same solid particle as the molecular encapsulating agent and the cyclopropene or they may be incorporated into separate solid particles or a combination thereof.

Some suitable additional compounds that may be included in dispersed particles (ii) are, for example, inert solid powders (i.e., powders that do not participate in the molecular encapsulating process and that do not react chemically with the other ingredients of the dispersed particles (ii)). Some suitable inert solid powders include, for example, carbohydrates such as, for example, dextrose. When inert solid powders are used, they may be present in an amount, by weight based on the weight of the dispersed particles (ii), that is more than 0% and that is 99% or less. In some embodiments, the amount of inert solid powders is 5% to 20%.

Further suitable additional compounds that may be included in dispersed particles (ii) are, for example, one or more amino acid salts, which, if present, may be present in an amount, by weight based on the weight of the dispersed particles (ii), that is more than 0% and that is 5% or less. In some embodiments, the amount of amino acid salts is 1% to 3%.

Further suitable additional compounds that may be included in dispersed particles (ii) are, for example, water, which, if present, may be present in an amount, by weight based on the weight of the dispersed particles (ii), that is more than 0% and that is 20% or less. In some embodiments, the amount of water is 1% to 9%.

In some embodiments of the present invention, the continuous phase (i) contains one or more dispersant (herein called "p-dispersant"). It is contemplated that some or all of p-dispersant is dissolved in the continuous phase (i), that some or all of the p-dispersant is located at the interfaces between the dispersed particles (ii) and the continuous phase (i) (i.e., on the surface of dispersed particles (ii)), or a combination thereof. Additionally, it is contemplated that some amount of p-dispersant (or none) may be located in one or more other places, such as, for example, at the surface of the continuous phase (i), on the walls of the container, in a complex with a molecular encapsulating agent, elsewhere in the composition, or a combination thereof.

Some suitable p-dispersants for use in continuous phase (i) are vinyl polymers. Some suitable p-dispersants are vinyl polymers that are homopolymers or that are statistical copolymers of two or more monomers. One suitable dispersant contains one or more polymer that has repeat units of the following structure:

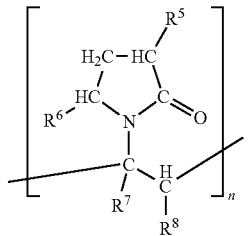

where each of $R^5$, $R^6$, $R^7$, and $R^8$ is an alkyl group, and n is 10 or larger. Such polymers are known as alkylated polyvinylpyrolidone. One suitable alkylated polyvinylpyrolidone is AGRIMER™ AL-22 dispersant from ISP Corp.

Other p-dispersants suitable for use in continuous phase (i) are polymers of polyethylene oxide attached to a hydrophobic group. Suitable hydrophobic groups include, for example, polypropylene oxide, polybutylene oxide, and polyhydroxystearic acid. Some suitable such p-dispersants include, for example, Atlox™ 4912 dispersant and Atlox™ 4914 dispersant, from Croda Corp.

In some embodiments, the pourable fluid (a) contains one or more dispersant (herein called "d-dispersants"). It is contemplated that some or all of d-dispersant is dissolved in the pourable fluid (a), that some or all of the d-dispersant is located at the interfaces between the droplets (b) and the pourable fluid (a) (i.e., on the surfaces of dispersed droplets (b)), or a combination thereof. Additionally, it is contemplated that some amount of d-dispersant (or none) may be located in one or more other places, such as, for example, at the surface of the pourable fluid (a), on the walls of the container, elsewhere in the composition, or a combination thereof.

One or more d-dispersants, if present, may have the same composition as one or more p-dispersants. In some embodiments, one or more d-dispersant is present that has composition different from any of the p-dispersants in the present invention. In some embodiments, one or more p-dispersant is present that has composition different from any of the d-dispersants in the present invention. In some embodiments, every p-dispersant is different from every d-dispersant.

Some suitable d-dispersants are vinyl polymers. Some suitable d-dispersants are vinyl polymers that are homopolymers or are statistical copolymers of two or more monomers. In some embodiments, one or more d-dispersant is used that is a copolymer of vinyl pyrolidone with vinyl acetate.

In some embodiments, one or more particulate mineral is present in the composition. In some embodiments, fumed silica is present. Fumed silica normally has median particle size of 5 to 50 nm. In some embodiments, the fumed silica that is present has been treated with dimethyldichlorosilane. Fumed silica, if present in the composition, may be present in one or both of the pourable fluid (a) and the continuous phase (i).

In some embodiments, the amount of p-dispersant, by weight based on the total weight of the dispersed droplets (b), is 0.2% or more; or 0.5% or more; or 1% or more. Independently, in some embodiments, the amount of p-dispersant, by weight based on the total weight of the dispersed droplets (b), is 5% or less; or 10% or less.

In some embodiments, the amount of solid particles (ii), by weight based on the total weight of the dispersed droplets (b), is 10% or more; or 20% or more; or 50% or more. Independently, in some embodiments, the amount of solid particles (ii), by weight based on the total weight of the dispersed droplets (b), is 80% or less; or 70% or less.

In some embodiments, the amount of droplets (b), by weight based on the total weight of the composition, is 5% or more; or 10% or more; or 20% or more. Independently, in some embodiments, the amount of droplets (b), by weight based on the total weight of the composition, is 70% or less; or 60% or less; or 50% or less; or 40% or less.

In some embodiments, the amount of particulate mineral that is present is, by weight based on the total weight of the composition, 0.2% or more; or 0.5% or more; or 1% or more; or 2% or more. Independently, in some embodiments, the amount of particulate mineral that is present is, by weight based on the total weight of the composition, 20% or less; or 10% or less; or 5% or less. In some embodiments, no particulate mineral is present.

In some embodiments, the amount of d-dispersant that is present is, by weight based on the total weight of the composition, 0.1% or more; or 0.2% or more; or 0.5% or more; or 1% or more. In some embodiments, the amount of d-dispersant that is present is, by weight based on the total weight of the composition, 10% or less; or 5% or less; or 2% or less.

Some suitable methods of putting the composition of the present invention to use involve placing the entire composition into water or an aqueous medium. In some embodiments, the composition is placed into an aqueous medium that contains water in the amount, by weight based on the weight of the aqueous medium, of 75% or more; or 90% or more; or 95% or more. In some of such embodiments, the amount of the composition is, by weight, based on the sum of the weights of the composition and the water or aqueous medium, 0.1% or more; or 0.2% or more; or 0.5% or more; or 1% or more; or 2% or more; or 5% or more; or 10% or more; or 20% or more. In some of such embodiments, the amount of the composition is, by weight, based on the sum of the weights of the composition and the water or aqueous medium, 80% or less; or 60% or less.

When it is intended to put the composition of the present invention into water, it is sometimes desirable to include an emulsifier in the composition of the present invention prior to mixing the composition of the present invention with the water. Some suitable emulsifiers include, for example, cationic surfactants, anionic surfactants, amphoteric surfactants, nonionic surfactants, and compatible mixtures thereof.

Some suitable anionic surfactants include, for example, those with anion selected from sulfates, sulfonates, carboxylates, and mixtures thereof. Some suitable cationic surfactants include, for example, those with quaternary ammonium cations. Some suitable amphoteric surfactants include, for example, betaines.

Some suitable nonionic surfactants, for example, are block copolymers. Some suitable block copolymers are, for example, butyl-based block copolymers. When an emulsifier is present in the composition of the present invention, the amount may be, for example, by weight based on the total weight of the composition, 0.5% or more; or 1% or more; or 5% or more. Independently, in some embodiments, the amount of emulsifier may be, for example, by weight based on the total weight of the composition, 15% or less; or 10% or less; or 7% or less.

When the composition of the present invention is put into water or an aqueous medium, it is sometimes desirable that some or all of the composition become dispersed in the water or aqueous medium. In some embodiments, some or all of the pourable fluid (a) may become dissolved in the water or aqueous medium, and the droplets (b) may become dispersed in the water or aqueous medium. In some embodiments, some or all of the pourable fluid (a) will become dispersed in the water or aqueous medium, either in discrete masses separate from the droplets (b) or in discrete masses that each contain some pourable fluid (a) and one or more droplet (b).

When the composition of the present invention is put into an aqueous medium, in some embodiments the amount of cyclopropene compound, by weight based on the total weight of the composition plus the aqueous medium, is 1 parts per million (ppm) or greater; or 10 ppm or greater. Independently, in some embodiments, the amount of cyclopropene compound, by weight based on the total weight of the composition plus the aqueous medium, is 1,000 ppm or lower; or 500 ppm or lower.

When a cyclopropene compound complex is used, direct contact between cyclopropene compound complex and water sometimes causes release of cyclopropene compound from the complex earlier than desired, and the cyclopropene compound may be lost (for example, through diffusion out of the composition, through chemical reaction, or a combination thereof). It is contemplated that, in the practice of those embodiments of the present invention in which the composition of the present invention is mixed with water, the cyclopropene compound complex remains in the solid particles (ii), so that contact between the cyclopropene compound complex and water is minimized or eliminated, and thus a desirably high fraction of the cyclopropene compound molecules of the composition remain in the composition for a time that is not undesirably short.

In some embodiments, the composition of the present invention is liquid over a temperature range of from 15° C. or lower to 30° C. or higher.

One possible use for the composition of the present invention is to treat plants or plant parts by bringing a composition of the present invention into contact with plants or plant parts.

Such contact may be accomplished in a variety of ways. For example, a composition of the present invention may be brought directly into contact with plants or plant parts. For another example, a composition of the present invention may be mixed with a diluent, and the resulting mixture may be brought directly into contact with plants or plant parts. In some embodiments, such a diluent may be water or an aqueous medium (as described herein above).

A liquid composition (which may be a composition of the present invention or a mixture of a composition of the present invention with a diluent) may suitably be brought into contact with plants or plant parts by any method, including, for example, spraying, dipping, drenching, fogging, and combinations thereof. Some suitable methods include spraying or dipping or a combination thereof. In some embodiments spraying is used. When spraying is used, it is contemplated that a liquid composition of the present invention is sprayed onto all or part of the surfaces of plants or plant parts. When dipping is used, it is contemplated that plant parts are dipped into a liquid composition of the present invention.

Plants that produce useful plant parts are known herein as "crop plants." Treatment may be performed on growing plants or on plant parts that have been harvested from growing plants. It is contemplated that, in performing the treatment on growing plants, the composition of the present invention may be contacted with the entire plant or may be contacted with one or more plant parts. Plant parts include any part of a plant, including, for example, flowers, buds, blooms, seeds, cuttings, roots, bulbs, fruits, vegetables, leaves, and combinations thereof.

Removal of useful plant parts from crop plants is known as harvesting. In some embodiments, crop plants are treated with composition of the present invention prior to the harvesting of the useful plant parts.

Suitable treatments may be performed on plants that are planted in a field, in a garden, in a building (such as, for example, a greenhouse), or in another location. Suitable treatments may be performed on a plants that are planted in open ground, in one or more containers (such as, for example, a pot, planter, or vase), in confined or raised beds, or in other places. In some embodiments, treatment is performed on plants that are in a location other than in a building. In some embodiments, plants are treated while they are growing in containers such as, for example, pots, flats, or portable beds.

Many of the plants that are suitable for use in the practice of the present invention can be usefully divided into categories or groups. One useful method for defining such groups is the "Definition and Classification of Commodities," published on or before Mar. 23, 2006, by the Food and Agriculture Organization ("FAO") of the United Nations as a "Draft."

In the practice of some embodiments of the present invention, it is contemplated to use plants that produce one or more crops that fall within any one of the following crop groups.

Crop Group 1 is cereals, including, for example, wheat, rice, barley, corn, popcorn, rye, oats, millet, sorghum, buckwheat, quiona, fonio, triticale, canary seed, canagua, quihuicha, adlay, wild rice, and other cereals. Crop Group 3 is sugar crops, including, for example, sugar cane, sugar beet, sugar maple, sweet sorghum, sugar palm, and other sugar crops. Crop Group 4 is pulses, including, for example, beans, chickpea, garbanzo, blackeyed pea, pigeon pea, lentil, and other pulses. Crop Group 5 is nuts, including, for example, brazil nuts, cashew nuts, chestnuts, almonds, walnuts, pistachios, hazelnuts, pecan nut, macadamia nut, and other nuts. Crop Group 6 is oil-bearing crops, including, for example, soybeans, groundnuts (including peanuts), coconuts, oil palm fruit, olives, karite nuts, castor beans, sunflower seeds, rapeseed, canola, tung nuts, safflower seed, sesame seed, mustard seed, poppy seed, melonseed, tallowtree seeds, kapok fruit, seed cotton, linseed, hempseed, and other oilseeds. In some embodiments, soybean plants are suitable. Crop Group 7 is vegetables, including, for example, cabbages, artichokes, asparagus, lettuce, spinach, cassava leaves, tomatoes, cauliflower, pumpkins, cucumbers and gherkins, eggplants, chilies and peppers, green onions, dry onions, garlic, leek, other alliaceous vegetables, green beans, green peas, green broad beans, string beans, carrots, okra, green corn, mushrooms, watermelons, cantaloupe melons, bamboo shoots, beets, chards, capers, cardoons, celery, chervil, cress, fennel, horseradish, marjoram, oyster plant, parsley, parsnips, radish, rhubarb, rutabaga, savory, scorzonera, sorrel, watercress, and other vegetables. Crop Group 8, is fruits, including, for example, bananas and plantains; citrus fruits; pome fruits; stone fruits; berries; grapes; tropical fruits; miscellaneous fruits; and other fruits. Crop Group 9 is fibers, including, for example, cotton, flax, hemp, kapok, jute, ramie, sisal, and other fibers from plants. In some embodiments, cotton plants are suitable. Crop Group 10 is spices. Crop Group 11 is Fodder crops. Fodder crops are crops that are cultivated primarily for animal feed. Crop Group 12 is stimulant crops, including, for example, coffee, cocoa bean, tea, mate, other plants used for making infusions like tea, and other stimulant corps. Crop Group 13 is tobacco and rubber and other crops, including, for example, plant oils used in perfumery, food, and other industries, pyrethrum, tobacco, natural rubber, natural gums, other resins, and vegetable waxes.

In some embodiments, the present invention involves treatment of any non-citrus plant (i.e., any plant that is not in the genus Citrus). In other embodiments, the practice of the present invention is limited to the treatment of non-citrus plants. Independently, in some embodiments, all the plants that are treated are not members of the genus Nicotiana.

In some embodiments, the composition of the present invention is used to treat crop plants growing in a field. Such a treatment operation may be performed one time or more than one time on a particular group of crop plants during a single growing season. In some embodiments, the amount of cyclopropene compound used in one treatment is 0.1 gram per hectare (g/ha) or more; or 0.5 g/ha or more; or 1 g/ha or more; or 5 g/ha or more; or 25 g/ha or more; or 50 g/ha or more; or 100 g/ha or more. Independently, in some embodiments, the amount of cyclopropene compound used in one spraying operation is 6000 g/ha or less; or 3000 g/ha or less; or 1500 g/ha or less.

Also contemplated are embodiments in which harvested plant parts are treated.

In some embodiments that involve addition of the composition of the present invention to water or aqueous medium, the water or aqueous medium contains one or more chelating agents. A chelating agent is a compound that contains two or more electron-donor atoms capable of forming two or more coordinate bonds with a metal atom.

In embodiments in which one or more chelating agent is used, suitable chelating agents include, for example, organic and inorganic chelating agents. In some embodiments, the chelating agent includes one or more aminocarboxylic acids, one or more salts thereof, one or more hydroxycarboxylic acids, one or more salts thereof, one or more oximes, or a mixture thereof. Some suitable aminocarboxylic acids include, for example, the neutral or salt forms of ethylenediaminetetraacetic acid (EDTA), hydroxyethylethylenediaminetriacetic acid (HEDTA), nitrilotriacetic acid (NTA), N-dihydroxyethylglycine (2-HxG), ethylenebis (hydroxyphenylglycine) (EHPG), and mixtures thereof.

Some suitable hydroxycarboxylic acids include, for example, the neutral or salt forms of tartaric acid, citric acid, gluconic acid, 5-sulfosalicylic acid, and mixtures thereof. Some suitable oximes include, for example, dimethylglyoxime, salicylaldoxime, and mixtures thereof. In some embodiments, the neutral or salt form of EDTA is used. In some embodiments, no metal-complexing agent is used.

It is to be understood that for purposes of the present specification and claims that, unless specifically stated otherwise, operations are performed at 25° C. at one atmosphere of pressure in air.

EXAMPLES

In the Examples below, the following materials were used:
Complex 1=Dry powder containing complex of 1-MCP and alpha-cyclodextrin, contained 4.7% 1-MCP by weight. Complex 1 was airmilled so that the median size as measured by the largest dimension was less than 50 micrometers.
HC01=ISOPAR™ V hydrocarbon, C12 to C20 petroleum hydrocarbons, from ExxonMobil Chemical.
PAVP=AGRIMER™ AL-22 dispersant, polymer of alkylated vinyl pyrolidone, ISP Corporation.
PVPVA=AGRIMER™ VA5I dispersant, copolymer of vinyl pyrolidone and vinyl acetate, ISP Corporation.
BCP=TOXIMUL™ 8320 emulsifier, butyl-based block copolymer, Stepan Co.
Silica 1=AEROSIL™ R972 silica, fumed silica, treated with dimethyldichlorosilane, particle size 5 to 50 nanometers, Evonik Industries.
PC=JEFFSOL™ AG-1550 solvent, contains propylene carbonate, Huntsman Performance Products.
Wax=paraffin wax, melting point 53-57° C., Aldrich Chemical.
Jelly=VASELINE™ petroleum jelly (manufactured by Unilever United States, available from Aldrich Chemical).
Soy=DRITEX™ S hydrogenated soybean oil, fully hydrogenated, Stratus Foods.
EVA=ELVAX™ 250 ethylene-vinyl acetate copolymer, DuPont.
HC02=UNIPAR™ 260 petroleum hydrocarbons, UniSource Energy, Inc.
"Base" (for Pourable Fluid (a))
2.50 g of Silica 1 and 55.51 g of PC were mixed and dispersed with a high shear mixer to form a suspension, which was heated to 60° C. to 70° C.

Comparative Example A

Droplet Formulation: 13.44 g of HC01 and 0.65 g of PAVP were mixed and heated to 60° C. to 70° C., whereon 21.50 g of Complex 1 was blended in. While still at 60 to 70° C., this Droplet Formulation was combined with Base (also at 60 to 70° C.) and dispersed with a high shear mixer until the viscosity appeared very thick. 1.4 g of PVPVA was added and the mixture was shaken by hand. Then 5.00 g of BCP was added and the mixture was shaken by hand. After addition of PVPVA and BCP, the viscosity appear to decrease somewhat. The resulting emulsion was allowed to cool to 25° C. This is a Comparative Example because HC01 is not a liquid of high viscosity at 25° C.

Examples 1-4

Compositions were made using the method of Comparative Example A, except that the 13.44 g of HCO1 was replaced with 13.44 g of a different ingredient as follows:

Example 1 used Wax (solid at 25° C.)
Example 2 used Jelly (liquid of high viscosity at 25° C.)
Example 3 used Soy (solid at 25° C.)
Example 4 used a solution of EVA in HCO2 (10% EVA by weight, based on the weight of the solution) (gel at 25° C.).

Observations:

Each example was diluted in propylene carbonate, and the result was observed with an optical microscope at magnification 400×. Additionally, each example was diluted in water, and the result was observed with an optical microscope at magnification of 400×. In every case, particles of Complex 1 were observed to be dispersed within droplets, and the droplets were observed to be dispersed throughout the field of view.

It was observed that the particles of Complex 1 were dispersed within droplets whose composition was the Droplet Formulation in each example.

The observations of the diluted formulations showed that each of Examples 1 to 4 had particles of Complex 1 that acted as solid particles (ii). These particles were dispersed within droplets made of the various Droplet Formulations, which acted as droplets (b). The droplets were dispersed within the propylene carbonate, which acted as pourable fluid (a).

We claim:

1. A composition comprising
(a) A non-aqueous pourable fluid,
(b) droplets dispersed in said pourable fluid (a), wherein said droplets comprise
  (i) a non-aqueous continuous phase that is a solid or that is a liquid of high viscosity and
  (ii) solid particles dispersed in said continuous phase (i), wherein
  the mass of the continuous phase (i) that is located in one droplet (b) will be isolated from other masses of continuous phase (i) that are located in other droplets (b) separated by the non-aqueous pourable fluid (a),
wherein said solid particles (ii) have median size as measured by the largest dimension of 100 micrometers or less, and
wherein said solid particles (ii) comprise one or more cyclopropene compound and one or more molecular encapsulating agent; wherein the mass of continuous phase (i) that is located in one droplet (b) will be isolated from other masses of continuous phase (i) that are located in other droplets (b), separated by said non-aqueous pourable fluid.

2. The composition of claim 1, wherein said pourable fluid (a) comprises one or more alkylene carbonate.

3. The composition of claim 1, wherein said pourable fluid (a) comprises one or more organic compounds with dipole moment of 2.5 debye or greater.

4. The composition of claim 1, wherein said continuous phase (i) comprises one or more organic compounds selected from the group consisting of hydrocarbons, non-hydrocarbon waxes, fatty compounds, mixtures containing organic polymers and organic fluids, and mixtures thereof.

5. The composition of claim 1, wherein said continuous phase (i) comprises one or more organic compounds with dipole moment of 1.5 debye or lower.

6. The composition of claim 1, wherein said continuous phase (i) is not soluble in said pourable fluid (a).

7. The composition of claim 1, further comprising water, wherein the amount of water is 50% or more by weight based on the weight of said composition.

8. A method of treating plants or plant parts comprising the step of contacting said plants or plants parts with the composition of claim 1.

9. The method of claim 8, wherein said method comprises the step of contacting said plant or plants parts with the composition of claim 7.

* * * * *

UNITED STATES PATENT AND TRADEMARK OFFICE
CERTIFICATE OF CORRECTION

PATENT NO. : 8,986,723 B2
APPLICATION NO. : 13/581532
DATED : March 24, 2015
INVENTOR(S) : Richard M. Jacobson et al.

It is certified that error appears in the above-identified patent and that said Letters Patent is hereby corrected as shown below:

In the Claims
In Claim 1, column 16, lines 45-49, after the word "agent," please delete the duplicative ";" and phrase:

"; wherein the mass of the continuous phase (i) that is located in one droplet (b) will be isolated from other masses of continuous phase (i) that are located in other droplets (b) separated by the non-aqueous pourable fluid"

such that the claim properly reads as follows:

1. A composition comprising
    (a) A non-aqueous pourable fluid,
    (b) droplets dispersed in said pourable fluid (a), wherein said droplets comprise
        (i) a non-aqueous continuous phase that is a solid or that is a liquid of high viscosity and
        (ii) solid particles dispersed in said continuous phase (i), wherein the mass of the continuous phase (i) that is located in one droplet (b) will be isolated from other masses of continuous phase (i) that are located in other droplets (b) separated by the non-aqueous pourable fluid (a),
            wherein said solid particles (ii) have median size as measured by the largest dimension of 100 micrometers or less, and
            wherein said solid particles (ii) comprise one or more cyclopropene compound and one or more molecular encapsulating agent.

Signed and Sealed this
Twenty-first Day of July, 2015

Michelle K. Lee
*Director of the United States Patent and Trademark Office*